(12) United States Patent
Shotton et al.

(10) Patent No.: US 10,182,883 B2
(45) Date of Patent: Jan. 22, 2019

(54) INSTRUMENTS AND COATINGS FORMED FROM A POROUS MATERIAL

(71) Applicant: DENTSPLY International Inc., York, PA (US)

(72) Inventors: Vincent Shotton, Broken Arrow, OK (US); Christopher Damien, Marietta, PA (US); Dan Ammon, Tulsa, OK (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 14/549,944

(22) Filed: Nov. 21, 2014

(65) Prior Publication Data

US 2015/0366635 A1 Dec. 24, 2015

Related U.S. Application Data

(60) Provisional application No. 61/906,688, filed on Nov. 20, 2013.

(51) Int. Cl.
*A61C 5/42* (2017.01)

(52) U.S. Cl.
CPC .......... *A61C 5/42* (2017.02); *A61C 2201/007* (2013.01); *Y10T 29/49568* (2015.01)

(58) Field of Classification Search
CPC .............. A61C 5/023; A61C 2201/007; Y10T 29/49568
USPC .......... 433/102, 224, 81, 665; 424/665, 102, 424/224, 81
See application file for complete search history.

(56) References Cited

U.S. PATENT DOCUMENTS

| | | | |
|---|---|---|---|
| 6,431,863 B1 | 8/2002 | Sachdeva et al. | |
| 2007/0054238 A1* | 3/2007 | Hof | A61C 3/02 433/102 |
| 2012/0093944 A1* | 4/2012 | Rokicki | A61B 17/12113 424/665 |
| 2012/0219927 A1* | 8/2012 | Maxwell | A61C 5/023 433/102 |

FOREIGN PATENT DOCUMENTS

| | | |
|---|---|---|
| DE | 102006007316 A1 | 8/2007 |
| WO | 2010030668 A1 | 3/2010 |

OTHER PUBLICATIONS

Schetky, et al. "Issues in the Further Development of Nitinol Properties and Processing for Medical Device Applications" from Sanjay Shrivastava (Jan. 1, 2004). Medical Device Materials: Proceedings from the Materials & Processes for Medical Devices Conference 2003, Sep. 8-10, 2003, Anaheim, California. ASM International, pp. 271-282.*
PCT International Search Report PCT/US2014/066780.
PCT Written Opinion PCT/US2014/066780.

* cited by examiner

*Primary Examiner* — Michael Carey
(74) *Attorney, Agent, or Firm* — Dentsply Sirona Inc.

(57) ABSTRACT

An endodontic instrument for cleaning/shaping a tooth root canal that includes an elongated shaft composed of a porous material, the shaft having a proximal end portion, a distal end and a tapered working portion having an external surface and a rotational axis, the working portion extending from the proximal end portion to the distal end.

26 Claims, 6 Drawing Sheets

INSTRUMENTS AND COATINGS FORMED FROM A POROUS MATERIAL

RELATED APPLICATIONS

This patent application claims the benefit of and priority to U.S. Provisional Patent Application Ser. No. 61/906,688, filed on Nov. 20, 2013, which is herein incorporated by reference for all purposes.

FIELD OF INVENTION

The present invention relates to endodontic instruments, and more particularly, instruments and/or coatings formed from a porous material.

BACKGROUND OF THE INVENTION

Endodontic instruments may be used for cleaning and enlarging the endodontic cavity space ("ECS"), also known as the root canal system of a human tooth. The unprepared root canal is usually a narrow channel that runs through the central portion of the root of the tooth. Cleaning and enlargement of the ECS may be necessitated by the death or necrosis of the dental pulp, which is the tissue that occupies that space in a healthy tooth. This tissue may degenerate for a multitude of reasons, which include tooth decay, deep dental restorations, complete and incomplete dental fractures, traumatic injuries or spontaneous necrosis due to the calcification and ischemia of the tissue, which usually accompanies the ageing process. Similar to a necrotic or gangrenous appendix, the complete removal of this tissue is paramount, if not urgent, because of the subsequent development of infections or dental abscesses, septicemia, and/or otherwise.

The root canal system of a human tooth is often narrow, curved and calcified, and may be extremely difficult to negotiate or clean. Indeed, the conventional endodontic or root canal instruments currently available are frequently inadequate in the complete removal of the pulp and the efficient enlargement of the ECS. Furthermore, they are usually predisposed to breakage, causing further destruction to the tooth. Broken instruments are usually difficult, if not impossible to remove, often necessitating the removal of the tooth. Injury to the tooth, which occurs as the result of a frank perforation or alteration of the natural anatomy of the ECS, may also lead to failure of the root canal and tooth loss.

The unprepared root canal of the tooth usually begins as a narrow and relatively parallel channel. The portal of entry or the orifice and the portal of exit or foramen are relatively equal in diameter. To accommodate complete cleaning and filling of the canal and to prevent further infection, the canal must usually be prepared. The endodontic cavity preparation ("ECP") generally includes progressively enlarging the orifice and the body of the canal, while leaving the foramen relatively small. The result is usually a continuous cone-shaped preparation.

In general, endodontic instruments are used to prepare the endodontic cavity space as described above. Endodontic instruments may include hand instruments and engine driven instruments. The latter may but need not be a rotary instrument. Combinations of both conventional hand and engine-driven rotary instruments are usually required to perform an ECP successfully and safely.

An endodontic instrument includes a shaft that includes a tip and a shank. The endodontic instrument also includes grooves that generally spiral around the shaft. The grooves are referred to in the instant specification as flutes as shown in FIG. 1 and FIG. 2, which is a cross-section of the endodontic instrument of FIG. 1.

With reference to FIGS. 1-2, an endodontic instrument (e.g., endodontic file), generally denoted as 10, has a shaft 12 tapered along at least a portion of its length 15 and terminating at a point 14. A portion of the shank above the tapered portion is illustrated as being substantially cylindrical. Helical flutes 16 are formed in the tapered portion 15 of the shaft 12 and define helical cutting edges 20.

The flutes are generally the spacing on both sides of a helical structure (or helix) that spirals around the shaft. The bottom portion of a flute—seen as a line or curve is referred to in the instant specification as a spline 22. The portion of a spline that comes into contact with the surface being cut during cutting will be referred to in the instant specification as a radial land 24. Generally, an instrument having right-handed cutting edges is one that will cut or remove material when rotated clockwise, as viewed from shank to tip 14. In this specification, a direction of rotation will be specified as viewed from the shank to the tip of the instrument. The cut direction of rotation for a right-handed endodontic instrument is clockwise. An instrument having left-handed cutting edges is one that will cut or remove material when rotated counter-clockwise. The cut direction of rotation, in this case, is counter-clockwise. An instrument may also reciprocate, or move forward and reverse and have either a right handed or left handed flute. In general, a reciprocating endodontic instrument will move in one direction further than the other with the handedness of the endodontic instrument being associated with the larger angle of rotation.

An endodontic instrument includes a working portion 26, which is the portion that may cut or remove material. The working portion is typically the portion along the shaft that is between the tip 14 of the instrument and the proximal end portion 28 of the flutes. The working portion is also referred to in this specification as the cutting portion, and the working length as the cutting or working length.

Hand instruments are typically manufactured from metal wire blanks of varying sizes. The metallurgical properties of these wires, in general, have been engineered to produce a wide range of physical properties. These wires are usually then twisted or cut to produce specific shapes and styles. Examples of hand instruments include K-type, H-type, and R-type hand instruments. The barbed broach is manufactured from soft iron wire that is tapered and notched to form barbs or rasps along its surface. These instruments are generally used in the gross removal of pulp tissue or debris from the root canal system. Another R-type file is a rat-tail file.

K-type instruments in current usage include reamers and K-files. K files are generally available in carbon steel, stainless steel, and more recently, an alloy of nickel-titanium. To fabricate a K-type instrument, a round wire of varying diameters is usually grounded into three or four-sided pyramidal blanks and then rotated or twisted into the appropriate shapes. These shapes are specified and controlled by the American National Standards Institute ("ANSI") and the International Standards Organization ("ISO"). The manufacturing processes for reamers and files are similar; except however, files usually have a greater number of flutes per unit length than reamers. Reamers are used in a rotational direction only, whereas files may be used in a rotational or push-pull fashion. Files made from three-sided or triangular blanks have smaller cross sectional areas than files made from four-sided blanks. Thus, these instruments are usually more flexible and less likely to fracture.

They also may display larger clearance angles and are more efficient during debridement. Triangular files, therefore, are generally considered more desirable for hand instrumentation.

H-type files are usually manufactured by grinding flutes into tapered round metal blanks to form a series of intersecting cones. H-type files may usually cut only in the pull direction (i.e., a pull stroke). Primarily because they have positive cutting angles, H-type files may be extremely efficient cutting instruments.

Hand instruments are usually manufactured according to guidelines of the ANSI and the ISO, which specified that a working portion of an instrument be 16 mm in length. ANSI and ISO further specified that a first diameter or $D_1$ of the instrument, be 1 mm from the tip or $D_0$. Other ANSI and ISO specifications require that: instruments have a standard taper of 0.02 mm per mm along the working portion; the tip maintain a pyramidal shape no greater than 75 degree in linear cross section; and hand instruments are available in 21, 25, and 31 mm lengths.

In addition to the hand instruments described above, there are rotary instruments that are usually motor driven. G-type drills are usually available in carbon or stainless steel. As is typical, the G-type drill 300 shown includes a short flame-shaped head attached to a long shank. The flutes, in this instance, have U-shaped splines. The instrument includes cutting edges that have negative rake-angles. In general, a rake angle is the angle between the leading edge of a cutting tool and a perpendicular to the surface being cut. Rake angle is further described below. The flame-shaped head includes a non-cutting surface to prevent perforation. The instrument may be used as a side-cutting instrument only. The instrument is relatively rigid and, therefore, cannot usually be used in a curved space, for example, the ECS.

SUMMARY OF INVENTION

The present invention seeks to improve upon prior endodontic instruments by providing improved endodontic instruments and/or process for manufacturing the endodontic instruments. In one aspect, the present invention provides an endodontic instrument for cleaning/shaping a tooth root canal, comprising: an elongated shaft composed of a porous material, the shaft having a proximal end portion, a distal end and a tapered working portion having an external surface and a rotational axis, the working portion extending from the proximal end portion to the distal end.

In another aspect, the present invention contemplates an endodontic instrument for cleaning/shaping a tooth root canal comprising: an elongated shaft having a proximal end portion, a distal end and a tapered working portion having a rotational axis, the working portion extending from the proximal end portion to the distal end; the external surface of the shaft working portion having a plurality of at least two flutes and a geometric cross section wherein the instrument is coated with a porous metal.

In another aspect, the present invention contemplates A method for forming an endodontic instrument comprising the steps of: providing a porous material have a porosity ranging from about 15% to about 90%; shaping the porous material to form the endodontic instrument, the endodontic instrument having a proximal end portion, a distal end and a tapered working portion having an external surface and a rotational axis, the working portion extending from the proximal end portion to the distal end.

In yet another aspect, any of the aspects of the present invention may be further characterized by one or any combination of the following features: wherein the porous material is a porous metal is selected from the group consisting of a Nitinol based material, a Copper based material, a titanium based material and a stainless steel based material; wherein the instrument has an axis of rotation that is centered such that the cross section center of mass (centroid) is located at the axis of rotation; wherein the instrument has an axis of rotation that is asymmetric such that the center of mass (centroid) is not located at the axis of rotation; wherein the external surface of the working portion includes a plurality flutes; wherein the external surface of the working portion is free of flutes; wherein the instrument is coated with a porous material; wherein the coated porous material is selected from the group consisting of a Nitinol based material, a Copper based material, a titanium based material and a stainless steel based material; wherein the endodontic instrument is a rotatable endodontic instrument; wherein the endodontic instrument is a reciprocating endodontic instrument; wherein the porous material is processed by high temperature, cold temperatures and/or strain; wherein the shaping step is selected from the group consisting of a grinding step, an additive manufacturing step, a three-dimensional printing step, an etching step, and combinations thereof; wherein the working portion includes a plurality of flutes; wherein the plurality of flutes are continual helical flutes; wherein the working portion is free of a flute; further comprising the step of coating at least a portion of the external surface with a porous coating; wherein the porous coating is a porous metal selected from the group consisting of a Nitinol based material, a Copper based material, a titanium based material and a stainless steel based material; wherein the shaping step including working the porous material under a strain to form the endodontic instrument; further comprising the step of heating treating and/or quenching the shaped endodontic instrument; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
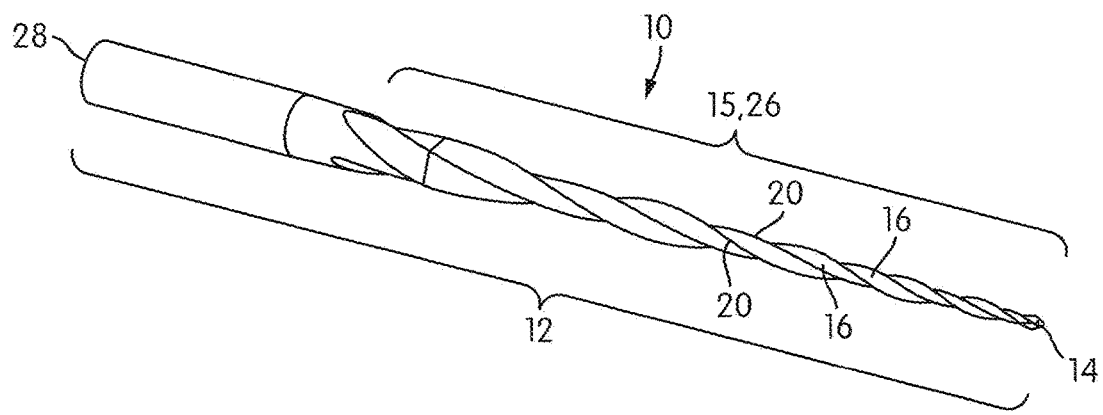
FIG. 1 is an perspective view of a typical endodontic instrument.
Figure 2:
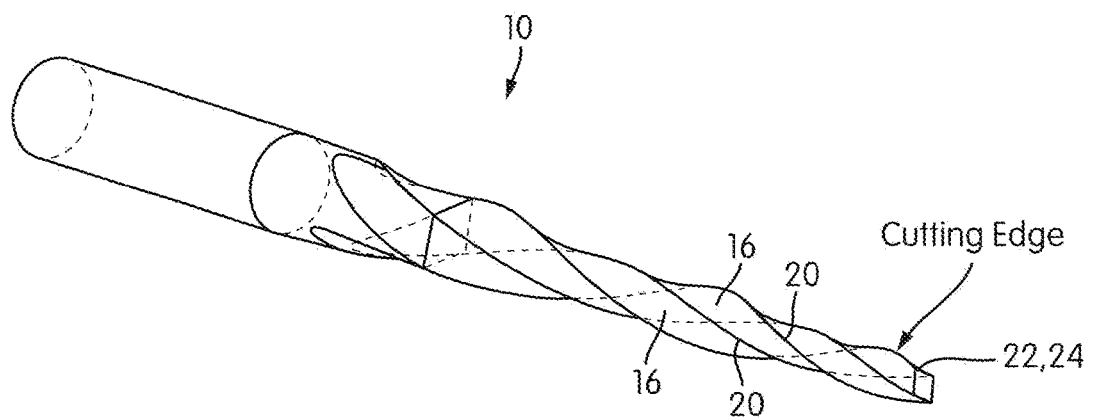
FIG. 2 is a cross-sectional perspective view of the endodontic instrument shown in FIG. 1.

The standard of care for endodontic instruments may be either a motor driven rotary file or a reciprocating motor driven file. When designing an endodontic instrument (e.g., endodontic file), many limitation need to be overcome. In particular, the movement of biological debris from the apex of the endodontic instrument to the coronal aspect of the endodontic instrument during RCT. If the transport of debris is limited, the endodontic instrument may become less efficient, become lodged, ledge or fracture. If biological debris is not transported efficiently, it could lead to greater amounts of smear layer. Smear layer is biologic debris that is "coated" on the dentinal walls via the endodontic instrument during RCT due to forces between the endodontic instrument and the canal wall. Smear layer is difficult to remove. If smear layer is not properly removed, it could lead to an unsuccessful RCT and/or a retreatment RCT. Current rotary endodontic instruments are primarily composed of nitinol. Typical endodontic files have helical features that scrape and remove the biological tissue during RCT. The design and file efficiency are limited by the surface area that the helixes contact. Although Nitinol is relatively robust, there are limits relative to design and material properties that result in endodontic file properties like cyclic fatigue, flexibility or peak torque that could be improved. Finally, when an endodontic file is fractured in the canal and cannot be removed, the apex of the root will contain biocompatible nitinol but the apex could remain open to the surrounding root area.

This invention discloses an endodontic instrument comprised of at least one porous metal, for example nitinol or nitinol derivatives (NiTiCr, NiTiCo, NiTiFe or NiTiX wherein X may be a third or more elements), copper based materials (e.g., CuZnAl or CuAlNi), stainless steel and other titanium derivatives. The endodontic instrument may be composed of porous Nitinol throughout the entire bulk of the endodontic instrument. It is appreciated that the endodontic instrument may be formed of a porous or non-porous material having a structure/design that includes a plurality of apertures of similar or various depths, wherein one or more of the plurality of apertures may include one or more second materials that may be a porous and/or non-porous material. When included, it is believed that weight distribution of a generally symmetrical endodontic instrument design along the axis of rotation may be varied such that during the rotation or reciprocation of the endodontic instrument the center of mass (centroid) is not located at the axis of rotation about a cross-section of a generally symmetrical instrument. Additionally, flexibility may be optimized by including multiple porous, non-porous, or combination of both materials in the endodontic instrument throughout the working portion or within one or more portions thereof to alter the flexibility of the endodontic instrument along the entire working portion or variably throughout the working portion at predetermined positions/locations radially and/or longitudinally about the endodontic instrument.

The endodontic instrument may have a helical design and/or may be conical without a helical design and/or have a variable taper. The porous nitinol may be a thin film coating on the surface of an endodontic instrument. The endodontic instrument may contain helixes and/or may be conical is design with no helixes and/or have a variable taper.

The endodontic instrument may also be composed of micron thick porous nitinol coating. The porous material (e.g., nitinol material) may be at least about 0.05 micron (e.g., 0.25 microns), typically at least about 0.5 micron, and preferably at least about 1 micron thick film coating (e.g., on the surface of an endodontic file). Furthermore, it is appreciated that the porous material may be less than about 500 microns (e.g., 250 microns, typically less than about 100 microns, and preferably less than about 50 microns, and more preferably less than 150 microns thick film coating. For example, the porous material may be provided in a range from about 0.05 microns to about 500 microns (e.g., about 0.25 microns to about 250 microns), typically from about 0.5 microns to about 100 microns, and preferably from about 1 micron to about 50 microns thick film coating.

It is appreciated that the porous coated may be formed and/or applied to the porous starting structure and/or the endodontic instrument using various procedures known in the art. Examples of procedures for forming and/or applying a porous coating to the porous starting structure and/or the endodontic instrument may include but are not limited to medical grade epoxy/glue, conventional sintering (CS), laser welding, laser melting, selective laser melting (SLM), laser sintering, selective laser sintering (SLS), self-propagating high-temperature synthesis (SHS), spark plasma sintering (SPS), hot isostatic pressing (HIP), capsule free HIP (CF-HIP), laser micro-holes punch, and otherwise.

Desirably, the porous material (e.g., nitinol) has a porosity of at least about 5%, typically at least about 15%, preferably at least about 25%, and more preferably at least about 35% (e.g., at least about 45%). Furthermore, the porous material may have a porosity of less than about 95%, typically less than about 90%, preferably less than 85%, and more preferably less than about 80% (e.g., less than about 75%). For example, the porous material may have a porosity ranging from about 5% to about 95%, typically from about 15% to about 90%, preferably from about 25% to about 85%, and more preferably from about 35% to about 80% (e.g., from about 45% to about 75%). Put a different way, the porous material preferably has a metal surface area or percentage of metal between about 20% and about 65% and more preferably between 25% and 55%.

The endodontic instrument may contain helixes and/or may be conical is design with no helixes and/or have a variable taper. The cross sections of the endodontic instrument containing or comprised of porous nitinol may be circular, oval, square, rectangular, rhombi, parallelogram, star design or contain concavities. The cross section may have an axis of rotation on the center of mass or have an axis of rotation that is off-centered with respect to the center of mass.

The invention disclosed above may solve many of the problems associated with endodontic instrument design and RCT. First, relative to the amount of surface that a porous surface provides relative to a traditional helical design is much higher, resulting in increased cutting efficiency. The increase in surface area or contact with the canal wall will also result in less smear layer formation. A porous endodontic instrument (e.g., file) or surface coated porous endodontic instrument will have to rely less on biological transport of material because the material may accumulate in the pores during RCT. If a porous nitinol instrument becomes lodged in the canal and cannot be removed, porous nitinol is known to form hydroxyapatite or bone. This will seal the apical region of the root canal.

Finally, an endodontic file composed of porous nitinol or coated with porous nitinol will contain less mass than an endodontic file designed similarly from tradition nitinol. This will result in improved cyclic fatigue and flexibility.

Figure 3:
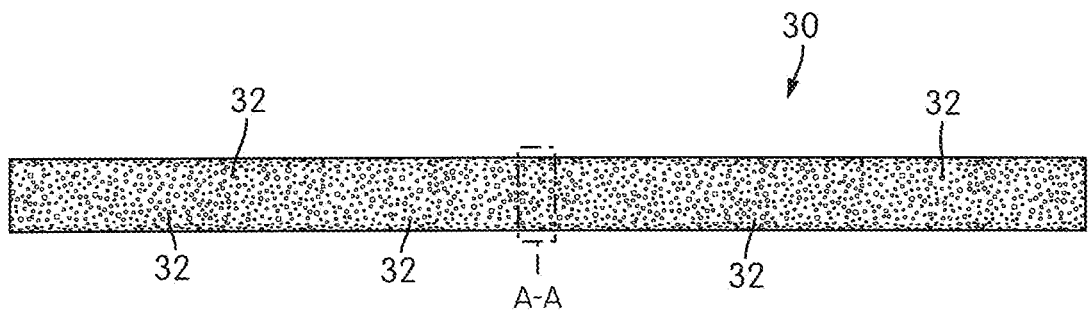
FIG. 3 is a top view of a porous starting structure according to at least one example embodiment of the present invention.
Figure 4:
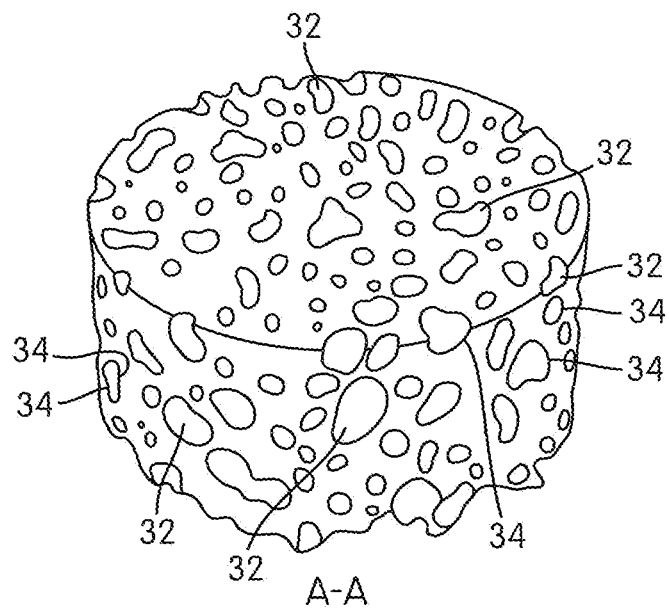
FIG. 4 is a zoomed-in perspective view in cross-section taken across A-A of the at least one example embodiment shown in FIG. 3.
Figure 5:
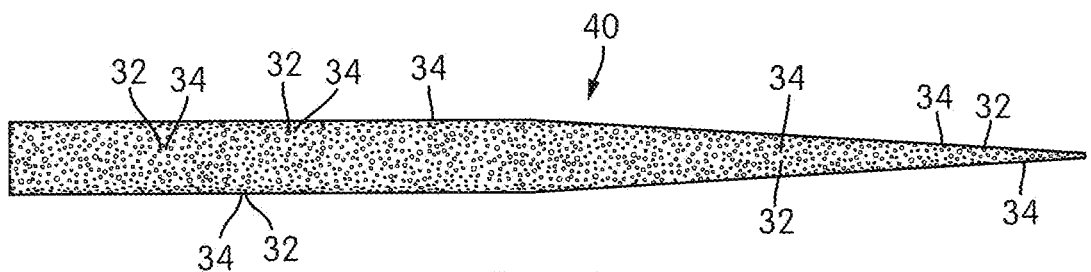
FIG. 5 is a top view of an endodontic instrument shaped from the porous starting pre-structure of FIG. 3 according to the least one example embodiment of the present invention.

The present invention contemplates forming endodontic instruments from porous starting (raw) structures. In one specific example as shown in FIG. 3, a porous wire 30 is provided. Desirably, the wire 30 may be shaped as an elongated cylindrical structure; however, other starting structures are contemplated. The starting porous structure includes one or more apertures 32 provided at various locations thereabout as shown in FIGS. 4-5. The apertures 32 may be located at similarly spaced or variable spaced positions about the structure. Furthermore, it is appreciated that the apertures 32 may be provided in shapes and/or sizes that are similar or different. Desirably, the starting porous structure may include a generally homogenous dispersion of apertures 32 throughout, though not required. As shown in FIG. 5, an endodontic instrument 40 is provided, which has been shaped by a manufacturing process (described herein) from the porous wire 30. In this specific example, the edges (e.g., along the external surface) of the apertures 32 act as cutting edges 34 for cleaning/shaping a tooth (e.g., root canal).

Figure 6:
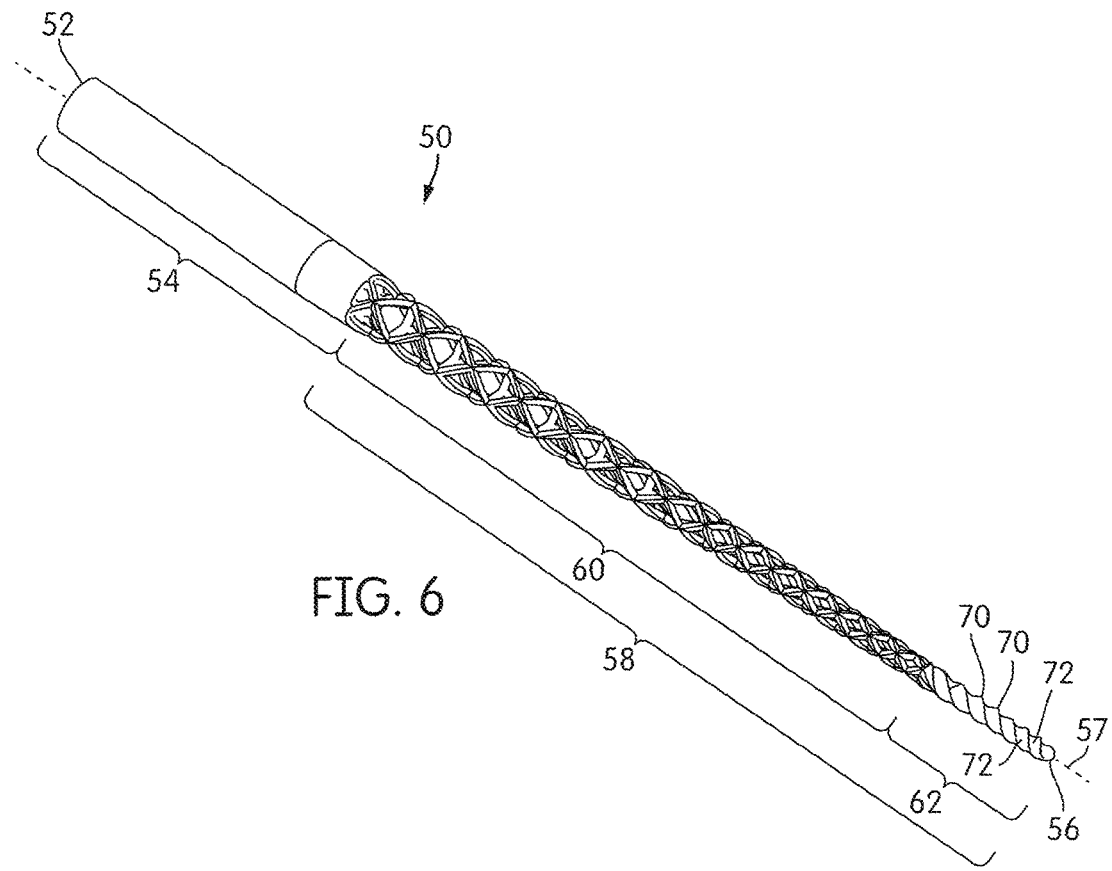
FIG. 6 is a perspective view of an endodontic instrument according to at least one example embodiment of the present invention.
Figure 7:
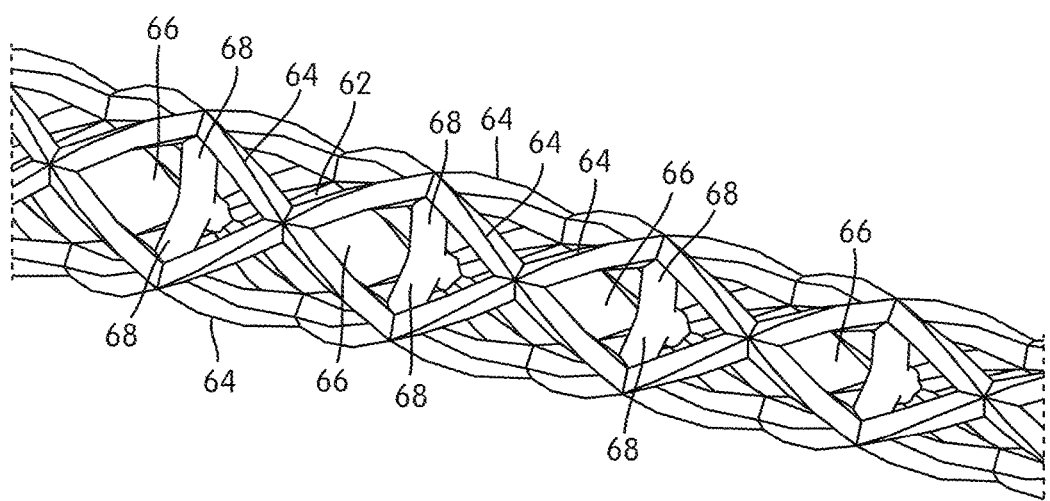
FIG. 7 is zoomed-in perspective view of the at least one example embodiment shown in FIG. 6.

FIGS. 6-7 show at least one example of another embodiment of the present invention, which provides for a hybrid endodontic instrument 50. The hybrid instrument 50 may include a proximal end 52, a proximal end portion 54, a distal end (e.g., tip) 56, a tapered working portion 58 that extends from the proximal end portion 54 to the distal end 56, and an instrument axis 57. The working portion 58 includes an intermediate portion 60 and a distal end portion 62. In one specific example, the intermediate portion 60 may include at least two (helical) cutting edges 64 that define apertures 66 and a generally lattice type structure. Desirably, the intermediate portion is substantially hollow and further includes internal supports 68 (FIG. 7) extending between the at least two cutting edges 64. Extending from the intermediate portion 60, the distal end portion may include at least two helical flutes 70, which may be formed as tapered portions and define at least two second-cutting edges 72. The second cutting edges 72 may extend from the cutting edges 64 or may be separate therefrom. Desirably, the distal end portion 62 may be substantially free of apertures 66 thereby forming a substantially solid (cutting) portion of porous material or non-porous material.

The cutting edges 64 and/or the internal supports 68 may include a width/thickness of at least about 1 microns (e.g., 25 microns), typically at least about 50 micron, and preferably at least about 100 microns (e.g., diameter or otherwise). Furthermore, it is appreciated that the cutting edges 64 and/or the internal supports 68 may be less than about 1000 microns (e.g., 800 microns), typically less than about 600 microns, and preferably less than about 500 microns, and more preferably less than 150 microns. For example, the cutting edges 64 and/or the internal supports 68 may include a width/thickness in a range from about 1 micron to about 1000 microns (e.g., about 25 microns to about 800 microns), typically from about 50 microns to about 600 microns, and preferably from about 100 micron to about 500 microns.

Figure 8:
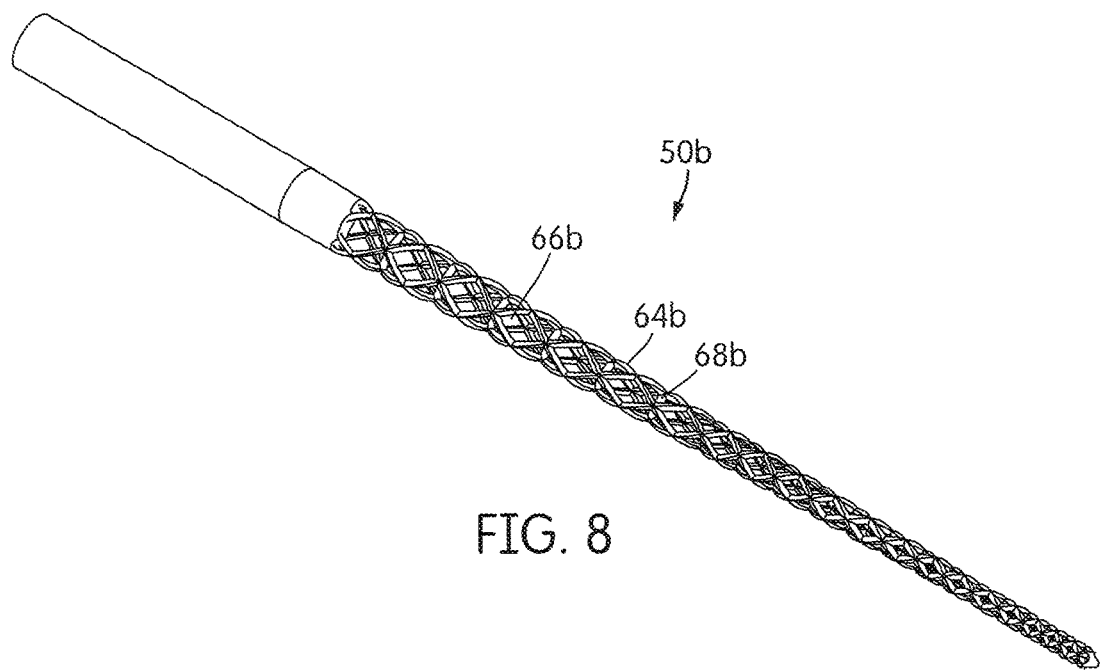
FIG. 8 is a perspective view of an endodontic instrument according to at least another example embodiment of the present invention.
Figure 9:
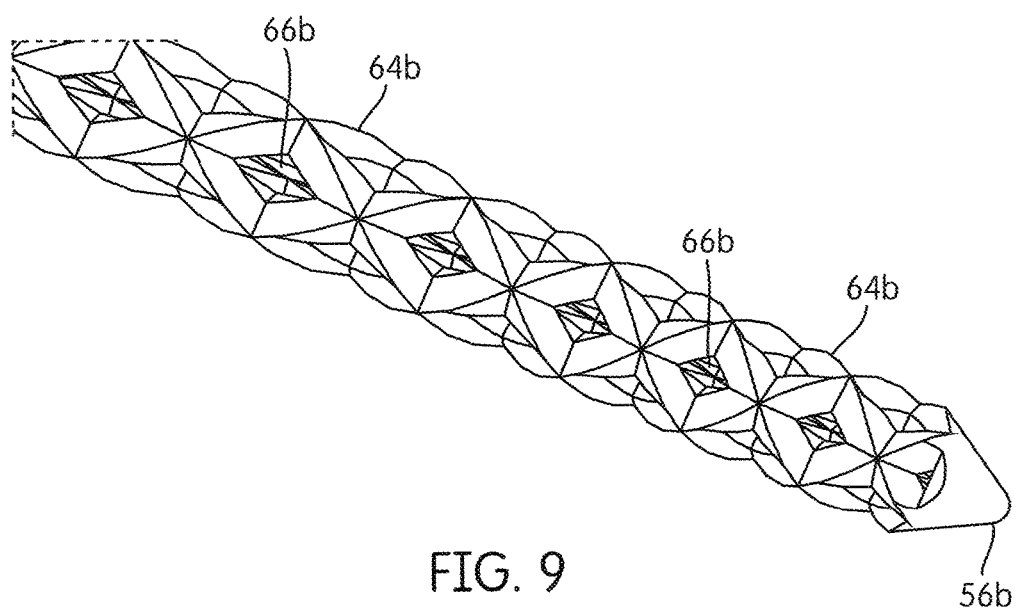
FIG. 9 is a zoomed-in perspective view of the at least another example embodiment shown in FIG. 8.
Figure 10:
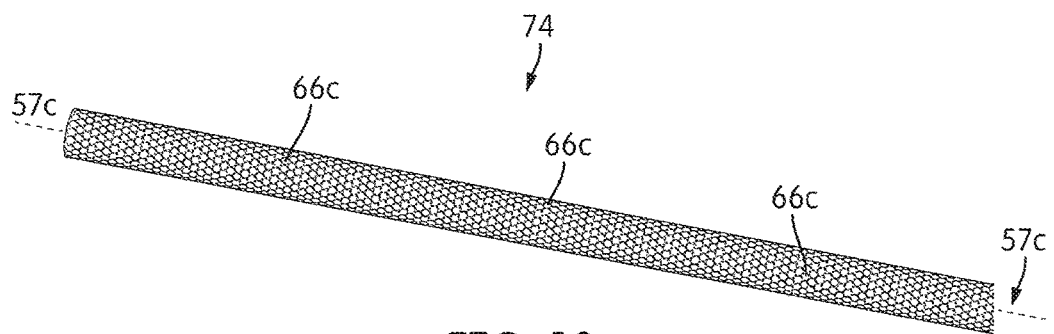
FIG. 10 is a perspective view of a starting material according to at least yet another example embodiment of the present invention.
Figure 11:
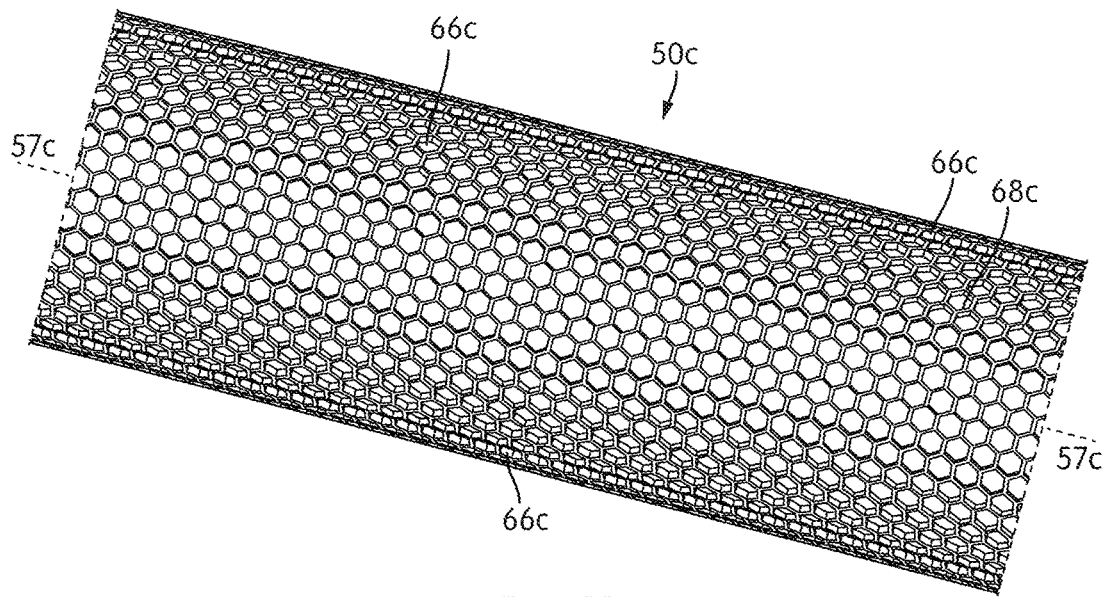
FIG. 11 is a zoomed-in perspective view of the at least yet another example embodiment shown in FIG. 10.

FIGS. 8-9 show another example of the present invention, which provides for a tapered endodontic instrument 50b. In this specific example, the cutting edges 64b of the intermediate portion 60b continue into and through the distal end portion 62b to the tip 56b. Desirably, both the intermediate portion and the distal end portion are substantially hollow with apertures 66b throughout. The cutting edges 64b extend along the working portion tapering towards an instrument axis 57b to the tip 56b. The tip 56b may be a substantially free of apertures thereby forming a substantially solid (cutting) portion of porous material or non-porous material FIGS. 10-11 show another embodiment of the present invention, which provide a porous (raw material) structure 74 for forming an endodontic instrument 50c (having a generally similar shape as endodontic instrument 40. In one specific example, the porous structure 74 may be a porous wire for forming an endodontic instrument such as an endodontic file. The porous structure may be formed of a porous material and/or a non-porous material. Apertures 66c may be provided as any various geometric shape, which may be the same shapes or different shapes of the same or different size throughout. In one specific embodiment, the apertures 66c may be of a hexagonal shape and of generally the same size to define a generally honeycomb lattice-type structure (e.g., honeycomb structure). In is appreciated that one or more of the 66c extend radially (at least partially or completely) to the instrument axis 57c. Additionally, it is appreciated that the porous structure 74 may include one or more layers separated by one or more internal supports 68c thereby defining longitudinal and/or radial apertures. When included, the apertures may be in alignment (radially) or offset (longitudinally parallel to the instrument axis) from layer to layer. It is appreciated that the porous (starting) structure 74 may thereafter be shaped to form an endodontic instrument by manufacturing process described herein.

Figure 12:
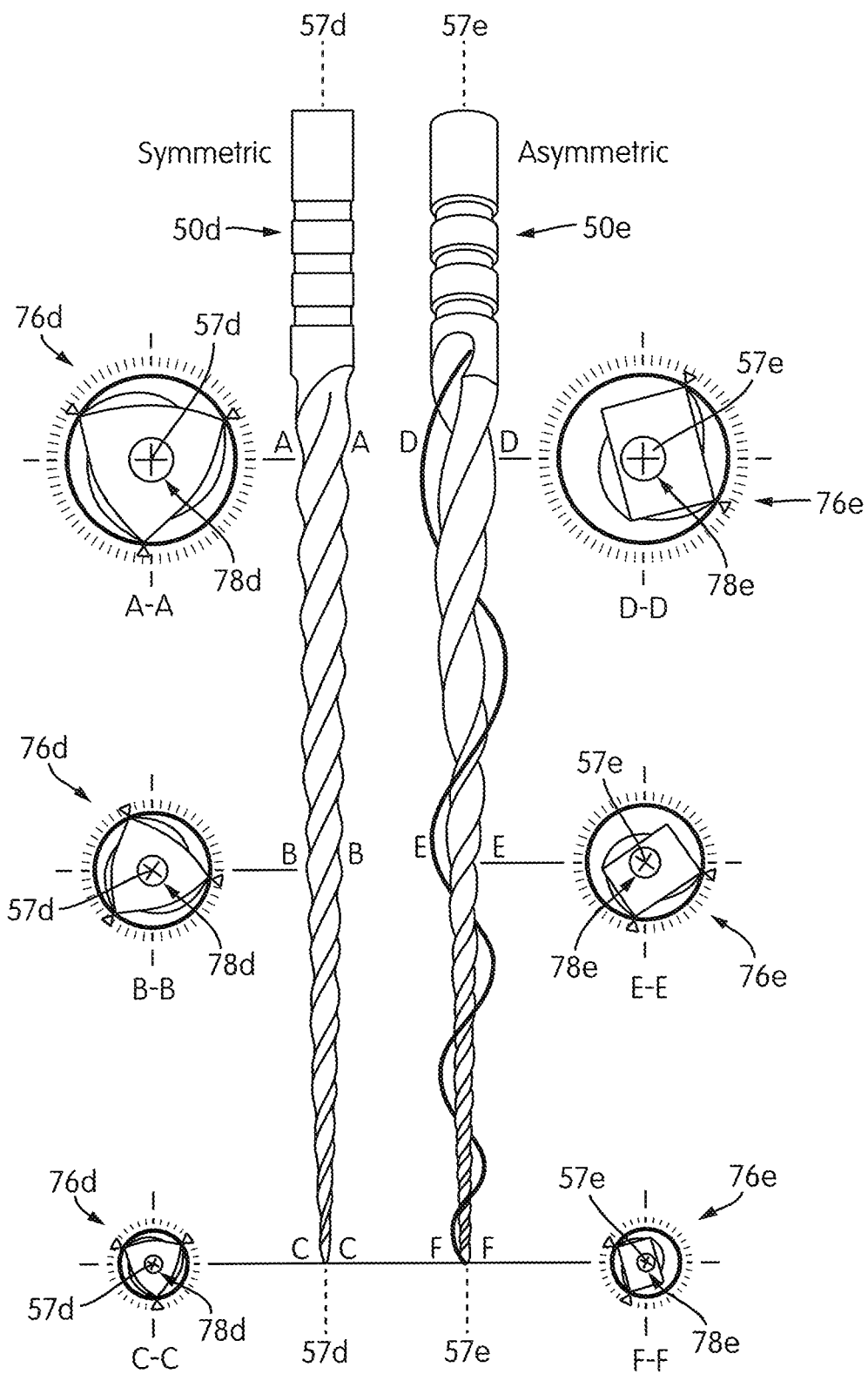
FIG. 12 is top view of at least two other example embodiments of the present invention.

FIG. 12 shows another embodiment of the present invention, which provides an endodontic instrument 50d and endodontic instrument 50e. Endodontic instruments 50d and 50e may be formed from a porous material and/or coated with a porous coating as described herein. It is appreciated that the structure of the endodontic instrument 50d may be generally symmetrical thereby having an axis of rotation 57d that is centered such that a first cross-section 76d (e.g., A-A, B-B, and/or C-C) has a center of mass 78d (centroid) that may be generally located about the axis of rotation 57d as compared to the structure of the endodontic instrument 50e that may be generally asymmetrical thereby having a second center of mass 78e (centroid) that may not be located about an axis of rotation 57e in a second cross-section 76e (e.g., D-D, E-E, and/or F-F). More particularly, it is believed that this first geometry (57d) can be symmetrical and the second geometry can be asymmetrical such that the first cross section 76d can be closer to the shank end than the tip end. The first cross section can have a different number of working surfaces than the second cross section. At the second cross section 76e, a second centroid 78e can be offset from the axis of rotation. The first geometry and the second geometry can include different numbers of working surfaces. The body can be flexible. The body can be sufficiently flexible such that when a tip of the body is bound at a fixed position as the body rotates or reciprocates, a portion of the body that intersects the second cross section bends away from the axis of rotation a substantially equal amount at a first angle of rotation and at a second angle of rotation. The first angle of rotation can be 180° from the second angle of rotation. The second cross section 76e can bend away from the axis of rotation 57e a substantially equally amount at each angle of rotation. A non-swaggering portion of the body can have a centroid 78d that lies substantially on the axis of rotation 57d and intersects the at least one working surface as the tip of the body is bound at a fixed position and the body rotates. The at least one working surface can include a cutting flute. A tip of the body may not have cutting surfaces. At a cross section that intersects the axis of rotation, a center of mass may be offset from the axis of rotation. The working surface can be configured to remove material when the body is rotated or reciprocated within a canal of the material. When the tip of the body is held in place and the body is rotated or reciprocated, at least a portion of the body may form helical waves.

Manufacturing

The porous metal file may be manufactured via traditional nitinol files where a metal wire is ground with the appropriate file design. In this case, a porous metal based wire would be ground. Also, traditional Nitinol wire could be etched to form a porous material. The porous file could also be manufactured by utilizing additive manufacturing techniques, for example, metal 3D printing or surface coatings.

Examples of porous materials and/or fabrication methods of porous materials may include, but are not limited to those described in Porous NiTi for bone implants: A review, (Bansiddhi, Sargeant, Stupp, and Dunand, which is herein incorporated by reference for all purposes.

In another embodiment, the present invention may provide various rotary file designs and/or raw materials that have posed difficulties while using traditional manufacturing techniques such as milling, turning, grinding, laser cutting, photochemical machining, etc. Advantageously, these difficulties may be substantially reduced or eliminated using an additive manufacturing technology otherwise known as 3D Printing, Rapid Prototyping, etc, and/or otherwise known additive technologies.

Manufacturing and/or shaping of the porous starting structure and/or the endodontic instrument may be achieved by known forming processes. Examples of such forming process include, but are not limited to 3D printing, additive manufacturing, and metal injection molding. 3D Printing and additive manufacturing are processes of making three-dimensional solid objects out of virtually any shape from a digital model. 3D printing is achieved using an additive process, where successive layers of material are laid down in different shapes. 3D printing is also considered distinct from traditional machining techniques, which mostly rely on the removal of material by methods such as milling, drilling, grinding, etc (subtractive processes). There are different types of additive processes where some melt or soften material to produce the layers such as selective laser melting, direct metal laser sintering, selective laser sintering, and fused deposition molding while other processes cure liquid materials such as stereolithography.

It is believed that one advantage to having a 3D printed rotary file may be that it allows for the design freedom in creating a product that is capable of achieving different functions while in the anatomy. For instance, FIG. 6 shows a hybrid design where the endodontic instrument may shape the root canal apically to allow irrigants to thoroughly clean the canal apically and provide for a shape for obturation while in the mid-root and coronal aspects, it is allowed to expand and collapse in order to allow the endodontic instrument to adapt to the natural anatomy. In this design, the 3D printer may print the solid metal blank apically and the stent type designs the remainder of the design. Conventional grinding processes may then be used to create the sharp edges and flutes which allows for a traditional file design apically.

Another way of using the 3D printing technology is to allow for the support of structures internally. For instance, in FIG. 7, it shows an example of internal struts to support the structure of the stent design. Other alternatives to support structurally design would be to vary the width and thickness of the different stent pieces to allow for more support or increased flexibility (thicker supports increase the stiffness while thinner supports provides for more flexibility).

FIG. 8 shows an example of being able to print a tapered endodontic instrument (e.g., stent file). In one specific example, a tubular stent design may be shaped by laser cut. By having a tube design, this prevents the design from being tapered initially and creates more stress on the stent design apically since it has to compress more to adapt to the apical aspect of the canal. By having a 3D printed tapered stent type design, it allows the endodontic instrument to have reduced stresses apically since there is less of a diameter and less compression required. FIG. 9 shows a zoomed-in view of this type of design such that the cutting tip may be closed/joined and allow the endodontic instrument to have more structure support apically versus an opened-ended/hollow tip design as described in U.S. Pat. No. 7,713,059, which are herein incorporated by reference for all purposes.

FIGS. 10 and 11 show how the raw material may be created using 3D printing and have the blank wire with porous surfaces. The porous raw material may then be ground to a desired tip and taper as a finished rotary file. The advantage to this type of design is that now the file has less core mass which increases its flexibility and cyclical fatigue resistance. It also provides for a rough surface as well as allows space for the cut material to go. Alternative types of designs for raw material embodiments are numerous but may include internal corrugated wire, random porosity of wire, a hollow tapered wire, etc.

There are many additive manufacturing techniques and many different types of materials used within these additive manufacturing techniques. Preferably, these designs are produced out of a metal material but they could be printed out of plastics as the technology develops. There are several types of metal 3D printing technologies including Direct Metal Laser Sintering, Electron Beam Melting, etc. The materials available with these technologies include: Cobalt Chrome, Titanium, Inconel, Nickel, Aluminum, Stainless Steel, Steel, etc. To our knowledge, Nickel Titanium is not a material currently available with these technologies but does not seem to be art issue in producing parts with these technologies.

It can be seen that the invention can also be described with reference to one or more of the following combinations.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a geometric cross section where the file is composed of porous metal.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having no spirals, a geometric cross section where the file is composed of porous metal.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a geometric cross section where the file is coated with a porous metal.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having no spirals, a geometric cross section where the file is coated with porous metal.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a geometric cross section where the file is etched to form a porous metal.

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having no spirals, a geometric cross section where the file is etched to form a porous metal.

An endodontic file, wherein the porous metal is composed of either a Nitinol based material, Cu based material, titanium based material or a stainless steel based material.

An endodontic file, wherein the material is processed by high temperature, cold temperatures and/or strain.

An endodontic file that has an axis of rotation that is centered such that the cross section center of mass (centroid) is located at the axis of rotation.

An endodontic file that has an axis of rotation that is asymmetric such that the center of mass (centroid) is not located at the axis of rotation.

An endodontic file wherein the material is processed by high temperature, cold temperatures and/or strain.

An endodontic file wherein the file is manufactured through a grinding process.

An endodontic file wherein the file is manufactured through an additive manufacturing process.

An endodontic file wherein the file is manufactured through an additive manufacturing process such as 3D printing or a coating technique.

An endodontic file wherein the file is manufactured through an etching manufacturing process.

The invention described herein has many other advantages. The endodontic instrument may have a single continuous flow path, which eliminates potential leak paths. Inherent stress concentrations may be reduced or substantially eliminated, thereby allowing the tip and/or the distal end portions to be reliable during vibration. The configuration of the tip and/or the distal end portions guide and transfer the ultrasonic vibration and energy in the planes of motion, which provides proper agitation to the irrigants. The tip assembly can also be disposable, thereby requiring that a new tip assembly be used for each patient and insuring that the tip assembly will be sterile prior to use.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Other foreseen embodiments or uses for the present invention include the use of the invention in the field of phacoemulsification, where a tip assembly such as the present invention may offer many advantages. Accordingly, it is intended that the invention be limited only by the scope of the appended claims.

The invention claimed is:

1. A porous endodontic instrument for cleaning/shaping a tooth root canal, comprising: an elongated shaft composed of a porous material, the shaft having a proximal end portion, a distal end; a tapered working portion and a rotational axis, the working portion extending from the proximal end portion to the distal end; wherein the working portion includes an intermediate portion and a distal end portion; wherein the intermediate portion includes plurality of apertures that define a generally lattice type structure; wherein the generally lattice type structure includes at least two cutting edges having an external surface and an internal surface defining an internal hollow space extending longitudinally; wherein the intermediate portion further includes at least one internal support extending between opposing portions of the internal surface and through the inner hollow space that is defined by the interior surface; wherein the porous endodontic instrument has a porosity ranging from about 25% and about 55% and wherein the at least one internal support has a thickness ranging from about 50 microns to about 600 microns.

2. The porous endodontic instrument according to claim 1, wherein the porous material is a porous metal being selected from the group consisting of a Nitinol based material, a Copper based material, a titanium based material and a stainless steel based material.

3. The porous endodontic instrument according to claim 2, wherein the instrument has an axis of rotation that is centered such that the cross section center of mass (centroid) is located at the axis of rotation.

4. The porous endodontic instrument according to claim 1, wherein the instrument has an axis of rotation that is asymmetric such that the center of mass (centroid) is not located at the axis of rotation.

5. The porous endodontic instrument according to claim 1, wherein the external surface of the working portion includes a plurality of flutes.

6. The porous endodontic instrument according to claim 1, wherein the external surface of the working portion is free of flutes.

7. The porous endodontic instrument according to claim 1, wherein the instrument is coated with a second porous material.

8. The porous endodontic instrument according to claim 7, wherein the second porous material is selected from the group consisting of a Nitinol based material, a Copper based material, a titanium based material and a stainless steel based material.

9. An endodontic instrument for cleaning/shaping a tooth root canal comprising: an elongated shaft having a proximal end portion, a distal end, a tapered working portion and a rotational axis, the working portion extending from the proximal end portion to the distal end; wherein the working portion includes an intermediate portion and a distal end portion; wherein the intermediate portion includes plurality of apertures that define a generally lattice type structure; wherein the generally lattice type structure includes at least two cutting edges having an external surface and an internal surface defining an internal hollow space extending longitudinally; wherein the intermediate portion further includes at least one internal support extending radially from the rotational axis and in between opposing portions of the internal surface and through the inner hollow space that is defined by the interior surface; the external surface of the shaft working portion having a plurality of at least two flutes and a geometric cross section; and wherein the instrument is coated with a porous material to form a porous coating, the porous coating having a thickness ranging from about 1 micron to about 50 microns and a porosity ranging from about 25% to about 55%.

10. The endodontic instrument according to claim 9 wherein the porous material is a porous metal that is selected from the group consisting of a Nitinol based material, a Copper based material, a titanium based material and a stainless steel based material.

11. The endodontic instrument according to claim 9, further comprising an axis of rotation that is centered such that at a cross-section, the center of mass is located at the axis of rotation.

12. The endodontic instrument according to claim 9, further comprising an axis of rotation that is asymmetric such that the center of mass is not located about the axis of rotation.

13. The endodontic instrument of claim 1, wherein the endodontic instrument is a rotatable endodontic instrument.

14. The endodontic instrument of claim 1, wherein the endodontic instrument is a reciprocating endodontic instrument.

15. The endodontic instrument according to claim 2, wherein the porous material is processed by high temperature, cold temperatures and/or strain.

16. A method for forming a porous endodontic instrument comprising the steps of:
providing a porous wire having a porosity ranging from about 25% to about 55%;
grinding the porous wire to form the porous endodontic instrument, the endodontic instrument having a proximal end portion, a distal end, a tapered working portion and a rotational axis, the working portion extending from the proximal end portion to the distal end, wherein the working portion includes an intermediate portion and a distal end portion; wherein the intermediate portion includes plurality of apertures that define a generally lattice type structure; wherein the generally lattice type structure includes at least two cutting edges having an external surface and an internal surface defining an internal hollow space extending longitudinally; wherein the intermediate portion further includes at least one internal support extending between opposing portions of the internal surface and through the inner hollow space that is defined by the interior surface; wherein the at least one internal support has a thickness ranging from about 50 microns to about 600 microns.

17. The method of claim 16, wherein the porous material is a porous metal selected from the group consisting of a Nitinol based material, a Copper based material, a titanium based material and a stainless steel based material.

18. The method of claim 16, wherein the shaping step is selected from the group consisting of a grinding step, an additive manufacturing step, a three-dimensional printing step, an etching step, and combinations thereof.

19. The method of claim 16, wherein the working portion includes a plurality of flutes.

20. The method of claim 19, wherein the plurality of flutes are continual helical flutes.

21. The method of claim 16, wherein the working portion is free of a flute.

22. The method of claim 16, further comprising the step of coating at least a portion of the external surface with a porous coating.

23. The method of claim 22, wherein the porous coating is a porous metal selected from the group consisting of a Nitinol based material, a Copper based material, a titanium based material and a stainless steel based material.

24. The method of claim 16, wherein the shaping step includes working the porous material under a strain to form the endodontic instrument.

25. The method of claim 16, further comprising the step of heat treating and/or quenching the shaped endodontic instrument.

26. The porous endodontic instrument according to claim 1, wherein at least one internal support extends radially from the rotational axis and in between the opposing portions of the internal surface.

* * * * *